United States Patent
Guth et al.

(10) Patent No.: US 6,387,233 B1
(45) Date of Patent: May 14, 2002

(54) POROUS ELECTRODE STRUCTURE FOR A GAS SENSOR AND SENSOR ARRANGEMENT

(75) Inventors: Ulrich Guth, Greifswald (DE); Klaus-Peter Sandow, Sint-Joris-Winge (BE); Dietrich Westphal, Greifswald (DE)

(73) Assignee: EPIQ Sensor-Nite N.V., Leuven (BE)

( * ) Notice: Subject to any disclaimer, the term of this patent is extended or adjusted under 35 U.S.C. 154(b) by 0 days.

(21) Appl. No.: 09/524,103

(22) Filed: Mar. 13, 2000

(30) Foreign Application Priority Data

Mar. 31, 1999 (DE) .......................... 199 14 628

(51) Int. Cl.⁷ ............................ G01N 27/407
(52) U.S. Cl. .................. 204/424; 204/427; 204/290.01
(58) Field of Search .................. 204/421–429, 204/290.01; 429/40, 218.1; 502/344, 346

(56) References Cited

U.S. PATENT DOCUMENTS

| | | | |
|---|---|---|---|
| 3,843,400 A | * 10/1974 | Radford et al. | 204/421 |
| 4,863,583 A | * 9/1989 | Kurachi et al. | 204/424 |
| 5,352,353 A | * 10/1994 | Schonauer et al. | 204/426 |
| 5,474,965 A | * 12/1995 | Nakatsuji et al. | 502/330 |
| 6,200,445 B1 | * 3/2001 | Yokota et al. | 204/424 |

FOREIGN PATENT DOCUMENTS

| | | |
|---|---|---|
| DE | 195 35 381 A1 | 4/1997 |
| DE | 197 01 493 C1 | 6/1998 |

OTHER PUBLICATIONS

Ishihara et al., Solid State Ionics 79 (1995), pp. 147–151. Month N/A.*

* cited by examiner

*Primary Examiner*—Robert J. Warden, Sr.
*Assistant Examiner*—Kaj K. Olsen
(74) *Attorney, Agent, or Firm*—Akin, Gump, Strauss, Hauer & Feld, L.L.P.

(57) ABSTRACT

A porous electrode structure for a gas sensor, as well as a sensor arrangement, is provided for detecting hydrocarbons in a measured gas. The porous structure guarantees, in addition to a low impedance, a high temporal stability and reproducibility of the measurement signal. The porous electrode structure has a conductive gold framework, which contains oxide components, in particular gallium oxide.

11 Claims, 2 Drawing Sheets

POROUS ELECTRODE STRUCTURE FOR A GAS SENSOR AND SENSOR ARRANGEMENT

BACKGROUND OF THE INVENTION

The invention relates to a porous electrode structure for a gas sensor as well as a sensor arrangement.

Gas sensors are known from German patent DE 197 01 493 C1, on the basis of semi-conducting gallium oxide for detection of reducing gases, such as hydrocarbons, hydrogen or even of solvents. There the gallium oxide layer lies on two electrically separated electrodes. With the reaction of reducing gases on the gallium oxide layer, their electrical resistance changes, which represents a measure for the concentration of the gas to be measured (hereinafter "measured gas"). By a covering of the gallium oxide layer with a non-continuous layer of gold islands, an increase in sensitivity to carbon monoxide is attained. The production parameters of the sensitive layer are hard to reproduce and decisively influence the measuring result.

From German published patent application DE 195 35 381 A1, electrode materials and sensor arrangements are known for the detection of hydrocarbons on the basis of lanthanide or rare earth compounds, which can be operated with the aid of an amperometric as well as a potentiometric measuring principle. Disadvantageous is the high impedance of these electrodes owing to their low electrical conductivity and, for example, the low adhesive capacity of the material on a solid electrolyte. In the description, electrodes of gold or gold alloys are also mentioned as sensitive layers for hydrocarbons, which have serious disadvantages. In addition to low stability over time, these electrodes of gold or gold alloys have a memory effect, which is dependent upon the preceding gas stresses and temperature cycles and makes a constant calibration necessary.

SUMMARY OF THE INVENTION

Underlying the invention is the object of making available an electrode structure as well as a sensor arrangement for detecting hydrocarbons, which, aside from a low impedance, guarantees a high temporal stability and reproducibility of the measurement signal.

The objective is accomplished by a porous electrode structure having a conductive gold framework, which contains oxide components. Surprisingly, a determinable memory effect does not arise here, as it does with hydrocarbon sensors having electrodes of gold or gold alloys. For the electrode structure of the invention, it is important that this have an open, i.e., permeable, porosity, wherein the electrical conductivity of the gold framework must furthermore be given in all spatial directions. The oxide components contained in the conductive gold framework can preferably have gallium oxide ($Ga_2O_3$). The gallium oxide therein should assume a proportion of 10–50 wt. %, preferably 30 wt. %, relative to the conductive framework. The oxide components can also contain, however, one or more oxygen ion-conducting solid electrolyte materials.

In the proposed sensor arrangements with at least one oxygen ion-conducting solid electrolyte, one measuring electrode arranged on a measured gas side and a counter electrode arranged on a reference gas side, the measuring electrode has a porous electrode structure with a conductive gold framework, which contains oxide components. This arrangement for a gas sensor is suited for detecting hydrocarbons in a measured gas.

In this connection, various oxygen ion-conducting solid electrolytes with different doping materials and supplemental amounts are usable, as well as mixtures thereof.

It proves to be especially advantageous if the oxide components of the hydrocarbon-sensitive measuring electrode contain gallium oxide. Here, the gallium oxide should assume a proportion of 10–50 wt. %, preferably of about 30 wt. %, relative to the conductive gold framework.

The oxide components for the measuring electrodes can also contain one or more oxygen ion-conducting solid electrolytes. Thus, for example, the adhesion or the coefficient of expansion between the oxygen ion-conducting solid electrolyte used and the electrode sensitive to hydrocarbons can be improved or adapted, if these are partially made of the same oxygen ion-containing material as the solid electrolyte used.

The potential measured between the measuring electrode and the counter electrode represents, with the presence of oxygen and hydrocarbons in the measured gas, a mixing potential which arises on the basis of different oxygen and hydrocarbon partial pressures between the measuring gas space and reference gas space. A change in the oxygen partial pressure in the measured gas accordingly leads to a change in the potential between the measuring electrode and the counter electrode. In order to be able to establish these possible changes of oxygen partial pressure in the measured gas, and to be able to separate the changes resulting therefrom in the measurement signal from the signal components which indicate changes in the hydrocarbon partial pressure in the measured gas, a comparison with a signal of an oxygen sensor arranged in the vicinity is expedient. The potential measured here on the basis of the various oxygen partial pressures in the measured gas and the reference gas can be deducted from the mixed potential between the measuring electrode and the counter electrode. There result in this case the signal components for which the hydrocarbon components in the measured gas are responsible.

Thus, further electrodes or electrode pairs of other materials can be arranged on the oxygen ion-conducting solid electrolyte which, together with the oxygen ion-conducting solid electrolyte, make possible a determination of the concentration of additional gases contained in the measured gas. This is expedient for obtaining a comparison signal, for example for establishing changes in the oxygen partial pressure in the measured gas, and spares the use of additional sensor arrangements.

With respect to the operating temperature of the measuring electrode of the invention, and also with an additional use of the oxygen ion-conducting electrolyte of the arrangement, for example for an oxygen sensor, a solid electrolyte material with sufficient oxygen ion conductivity must be used. The ideal temperature range for the use of the above-described, hydrocarbon-sensitive measuring electrode in a sensor arrangement lies in the range of 600 to 700° C. If this temperature range is not present or stably guaranteed at the place of operation, then the use of heater elements is necessary. It is advantageous here if an electric heater element is arranged directly on the oxygen ion-conducting electrolyte, whereby between solid electrolyte and heater element one or more insulating layers must be arranged. Here, attention must also be paid in particular to an electrical insulation between the heater element and the electrodes of the gas sensor. Of course, electric heater elements can also be arranged spaced from the oxygen ion-conducting solid electrolyte.

DESCRIPTION OF SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
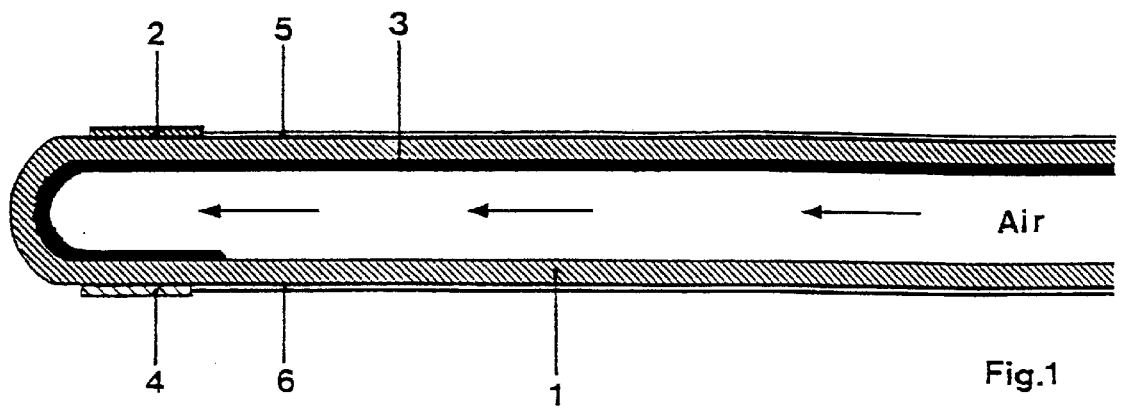
FIG. 1 is longitudinal sectional view of a sensor arrangement according to the invention for detecting hydrocarbons and oxygen.

FIG. 1 shows a possible sensor arrangement with a potentiometric measuring principle for detection of hydrocarbons using the electrode structure of the invention for use in the exhaust gas of a motor vehicle. The oxygen ion-conducting solid electrolyte 1 is here constructed in the form of a tube closed at one end and serves at the same time as a carrier for electrodes 2, 3 and 4. The solid electrolyte 1 can be configured as bulk material in further constructive embodiments, as well as be constructed as a non-bearing layer on a separate carrier structure.

As a material with oxygen ion-conducting properties, zirconium oxide or cerium oxide, for example, can be used, which is doped with different supplemental amounts of magnesium, calcium, yttrium, scandium or rare earth elements, for example erbium or gadolinium, for increasing the oxygen ion conductivity. However, other oxygen ion-conducting compounds, for example on the basis of $LaGaO_3$, are usable. The interior of the solid electrolyte tube 1 is flushed with a reference gas, for example with air, while the exterior of the solid electrolyte tube 1 is situated in the measured gas, which contains hydrocarbons. The measured gas side and the reference gas side must be separated gas tight from one another. This separation is not represented here.

The hydrocarbon-sensitive measuring electrode 2 of the invention is applied on the solid electrolyte tube 1 on the measured gas side, in this embodiment in thick layer technology. The measuring electrode 2 is contacted with a conductive path 5. In the interior of the solid electrolyte tube 1 the counter electrode 3 is located on the reference gas side. The measuring electrode 2 and the counter electrode 3 form an electrode pair, which makes possible the tapping of the appearing mixed potential. A further electrode 4, contacted with the conductive path 6, is applied on the solid electrolyte tube 1 in the measured gas space. This electrode 4, for example made of platinum, forms a second electrode pair with the counter electrode. The potential measured here on the basis of the different oxygen partial pressures in the measured gas and reference gas is deducted from the mixed potential of the first electrode pair.

Figure 2:
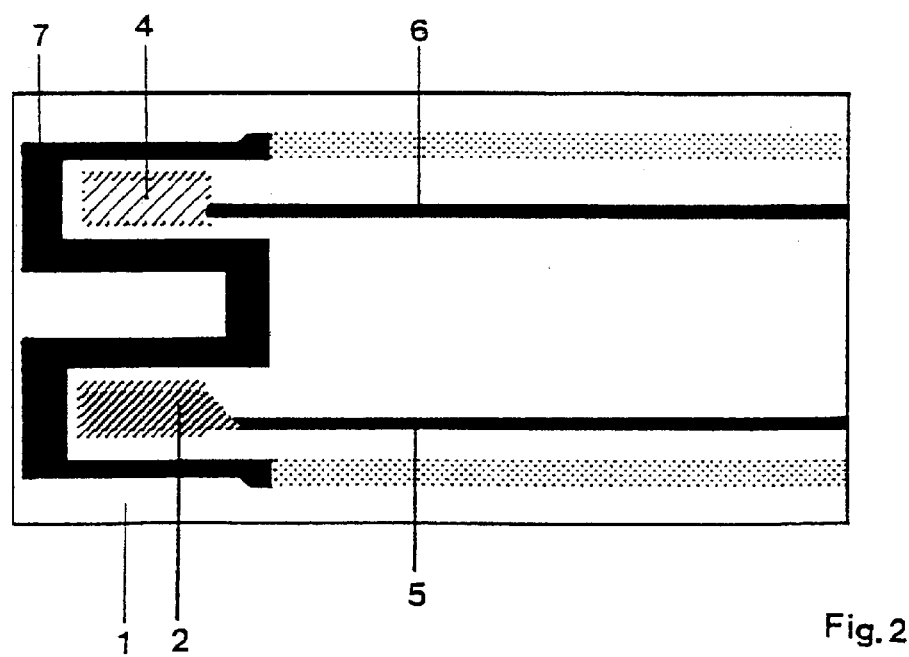
FIG. 2 is a plan view of the sensor arrangement according to FIG. 1, wherein the tubular sensor arrangement has been unwound to illustrate the construction of the electrode and heating layers by thick layer technology.

FIG. 2 shows the unwound jacket surface of the solid electrolyte tube 1 and the electrode layers arranged in thick layer technology on the outer surface. The hydrocarbon-sensitive measuring electrode 2, contacted with the conductive path 5, is arranged directly on the solid electrolyte tube 1. The oxygen-sensitive only electrode 4, contacted with conductive path 6, is likewise situated at a distance on the measured gas side of the solid electrolyte tube 1. In order to attain the optimal operating temperature of the sensor arrangement rapidly and to maintain it stably, an electrical heater element 7, here in the form of a meander, is arranged near the electrodes on the measured gas side.

Figure 3:
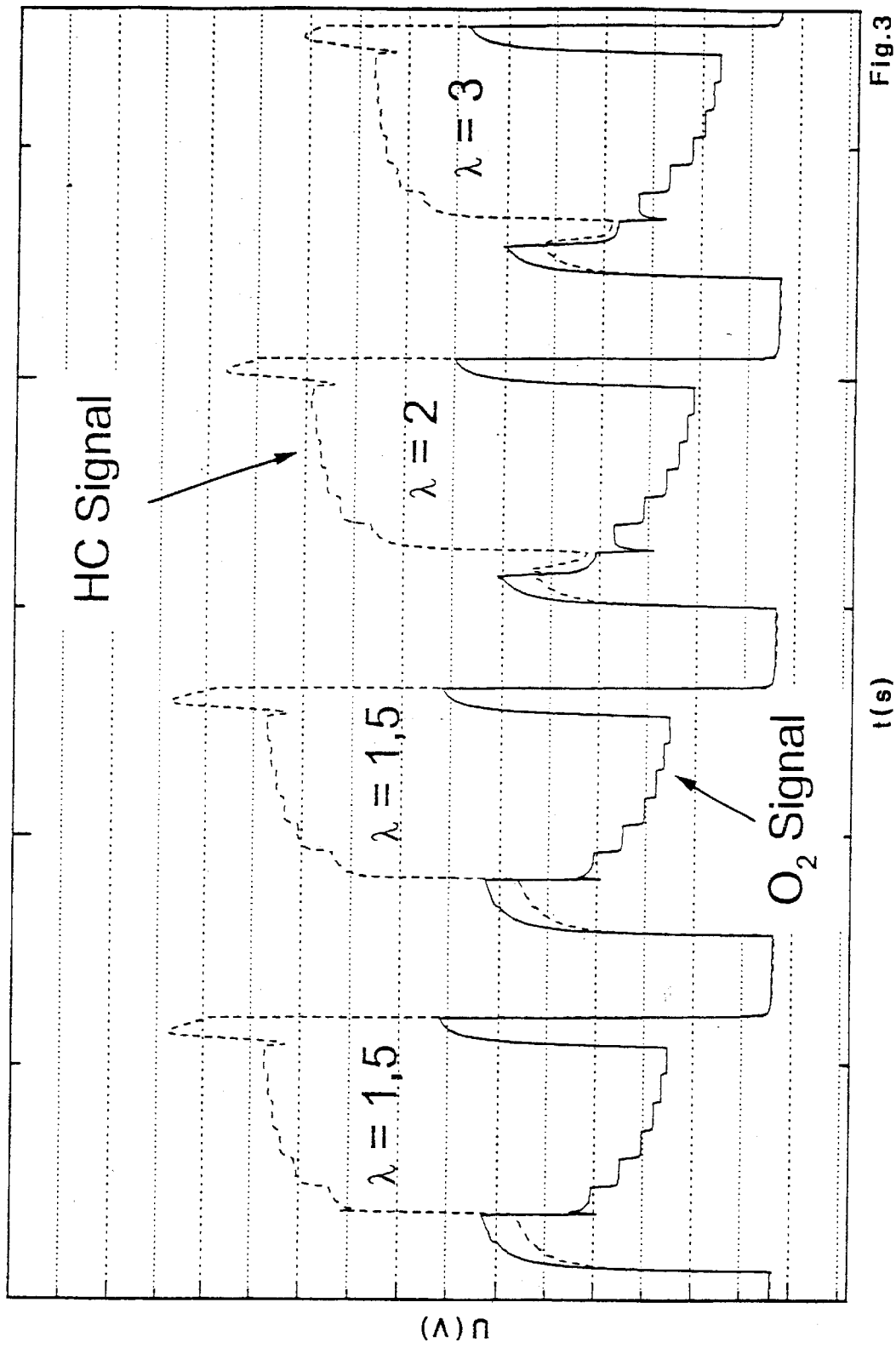
FIG. 3 is a series of graphical representations of the response behavior of the sensor arrangement in various hydrocarbon-containing measured gas mixtures, with voltage signals (HC and $O_2$) of the electrode pairs plotted over time.

FIG. 3 shows the response behavior of the sensor arrangement in hydrocarbon-containing measured gas. In the diagram are plotted over time the voltage signals of the first electrode pair, sensitive to changes in the amount of hydrocarbons in the measured gas (HC signal), and those of the second electrode pair, sensitive to changes in the amount of oxygen in the measured gas ($O_2$ signal). Here, the electrodes in the measured gas were contacted with different measured gas mixtures with lambda values λ in the range of 1.5 to 3. The lambda value corresponds to the relationship between the amount of air/amount of fuel used and the stoichiometric amount of air/amount of fuel, wherein lambda values smaller than 1 correspond-to rich or reducing measured gas combinations, and lambda values greater than 1 correspond to lean or oxidizing measured gas combinations.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A porous electrode structure for a gas sensor, wherein the structure comprises a conductive gold framework, wherein said framework comprises a group of oxide components, wherein the group of oxide components comprises gallium oxide, $Ga_2O_3$.

2. The porous electrode structure according to claim 1, wherein the gallium oxide assumes a proportion of 10–50 wt. % in relation to the conductive gold framework.

3. The porous electrode structure according to claim 2, wherein the proportion of gallium oxide is about 30 wt. % of the conductive gold framework.

4. The porous electrode structure in accordance with claim 1, wherein the oxide components contain one or more oxygen ion-conducting-solid electrolyte materials.

5. A sensor arrangement comprising at least one oxygen ion-conducting solid electrolyte (1), a measuring electrode arranged on a measured gas side of the arrangement and a counter electrode arranged on a reference gas side of the arrangement, wherein the measuring electrode (2) has a porous electrode structure comprising a conductive gold framework, wherein said framework comprises a group of oxide components, wherein the group of oxide components comprises gallium oxide, $Ga_2O_3$.

6. The sensor arrangement according to claim 5, wherein the gallium oxide assumes a proportion of 10–50 wt. % in relation to the conductive gold framework.

7. The sensor arrangement according to claim 6, wherein the proportion of gallium oxide is about 30 wt. % of the conductive gold framework.

8. The sensor arrangement according to claim 5, wherein the oxide components of the measuring electrode (2) contain one or more oxygen ion-conducting solid electrolyte materials.

9. The sensor arrangement according to claim 5, wherein further electrodes or electrode pairs are arranged on the solid electrolyte (1).

10. The sensor arrangement according to claim 5, wherein an electric heater element (7) is arranged on the solid electrolyte (1).

11. The sensor arrangement according to claim 5, wherein an electric heater element is arranged at a distance from the solid electrolyte (1).

* * * * *